United States Patent [19]

Griffith

[11] Patent Number: 5,093,524

[45] Date of Patent: Mar. 3, 1992

[54] 2-(ALKYLAMINO)ACETAMIDE DERIVATIVES

[75] Inventor: Ronald C. Griffith, Pittsford, N.Y.

[73] Assignee: Fisons Corporation, Bedford, Mass.

[21] Appl. No.: 598,585

[22] Filed: Oct. 15, 1990

[51] Int. Cl.$^5$ ............................................. C07C 237/07
[52] U.S. Cl. ..................................... 564/190; 564/196
[58] Field of Search ................ 564/190, 196; 514/624, 514/626

[56] References Cited

U.S. PATENT DOCUMENTS 2,449,618  9/1948  Bruce ............................... 564/212 X
4,073,941  2/1978  Lindberg et al. ............... 564/212 X

FOREIGN PATENT DOCUMENTS 955508   of 1957  Fed. Rep. of Germany.
343388   of 1960  Switzerland.
1420067  1/1976   United Kingdom ................ 564/157

OTHER PUBLICATIONS

CA 64,14162f.
CA 73,25044n.
CA 77,19586g.
CA 85,5705y.
CA 96,19744z.
Beilstein's Handbuch der Organischen Chemie, 4th ed., 3rd supp., (1973), Springer Publications, pp. 3265 and 3276.
Patel et al., J. Indian Chem. Soc., vol. 49, No. 2, 1972, pp. 177–180.

Primary Examiner—Carolyn Elmore
Attorney, Agent, or Firm—Seidel, Gonda, Lavorgna & Monaco

[57] ABSTRACT

Compounds are provided of the following general structure:

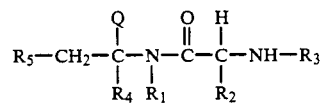

wherein $R_4$ is lower alkyl ($C_1$–$C_4$); $R_1$ is hydrogen or methyl, $R_2$ is hydrogen or methyl, $R_3$ is lower alkyl ($C_1$–$C_6$) or cyclopropyl, and where $R_5$ and Q are independently selected from phenyl or 4-fluorophenyl. They are useful for providing sedative and antiepileptic activity.

15 Claims, No Drawings

2-(ALKYLAMINO)ACETAMIDE DERIVATIVES

This is a continuation of co-pending application Ser. No. 145,865 filed on Jan. 20, 1988, now abandoned.

SUMMARY OF THE INVENTION

Novel substituted 2-aminoacetamide derivatives have been prepared and found to possess useful sedative and especially antiepileptic activity.

GENERAL DESCRIPTION

This invention relates to novel 2-aminoacetamide compounds of the following general structure (1):

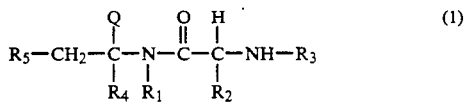

wherein $R_4$ is lower alkyl ($C_1$–$C_4$); $R_1$ is hydrogen or methyl, $R_2$ is hydrogen or methyl, $R_3$ is lower alkyl ($C_1$–$C_6$) or cyclopropyl, and where $R_5$ and Q are independently selected from phenyl or 4-fluorophenyl.

This invention also relates to diastereomers, optical isomers and mixtures thereof and to pharmaceutically acceptable acid addition salts of the compounds of general formula (1).

Compounds of this invention possess useful pharmaceutical properties. In particular they possess sedative and antiepileptic properties. Especially useful compounds are those in which $R_4$ is methyl and $R_5$ and Q are phenyl.

DETAILED DESCRIPTION

The 2-aminoacetamides of general formula (1) as described fully above are conveniently prepared and by suitable amide bond forming reactions from the corresponding amine intermediates of general formula (2):

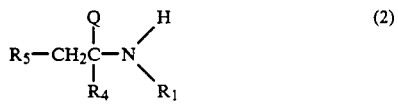

where $R_4$ is lower alkyl ($C_1$–$C_4$), $R_1$ is hydrogen or methyl, and where $R_5$ and Q are independently selected from phenyl or 4-fluorophenyl and optical isomers thereof. Most of the amines of general formula (2) are known compounds and may be purchased commercially or conveniently prepared by suitable modifications of the reported procedures. Some of the amines (2) are not known, but are prepared by similar procedures. The preparation of the non-commercially available amines of general formula (2) is described in the "Preparation of Intermediates" Section.

Many amide bond forming reactions may in principle be utilized for the conversion of the amines of general formula (2) to the amides of general formula (1). Two procedures which represent the preferred methods for this conversion are designated Method A and Method B.

Method A consists of direct coupling of suitably protected amino acid derivatives of formula (3):

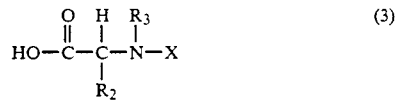

where X is a urethane protecting group preferably benzyloxycarbonyl (CBZ) or t-butyloxycarbonyl (BOC), with an amine of general formula (2), in an inert solvent in the presence of a coupling reagent such as dicyclohexylcarbodiimide with or without 1-hydroxybenzotriazole or other additives to provide coupled products of general formula (4):

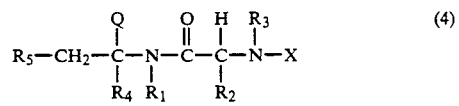

The protecting groups X, are then readily removed by either catalytic hydrogenation for the CBZ groups or treatment with an acid such as trifluoroacetic or hydrochloric acid for the BOC group to provide the compounds of general formula (1).

Method B consists of reacting an amine of general formula (2) with an activated two carbon acid derivative which contains a leaving group alpha to the carbonyl, such as chloroacetyl chloride, in the presence of an acid acceptor, such as triethylamine, to produce the corresponding 2-chloroacetamide derivative of general formula (5):

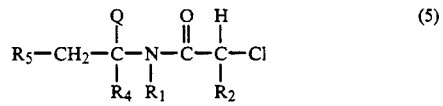

Such an intermediate can be directly reacted with amines ($R_3NH_2$) in a solvent such as a lower alkanol, for example methanol or ethanol, or a chlorinated solvent, for example chloroform or methylene chloride or mixtures thereof to provide the corresponding compounds of the general formula (1).

The compounds of general formula (1) possess asymmetric centers, and therefore optical isomers and diastereomeric forms are possible. Such compounds are conveniently prepared from optically active amines of formula (2) and/or optically active protected amino acid of formula (3) by the methods described above.

The compounds of general formula (1) are basic compounds and may be used as such or pharmaceutically acceptable acid addition salts may be prepared by treatment with various inorganic or organic acids, such as hydrochloric, hydrobromic, sulfuric, phosphoric, acetic, lactic, succinic, fumaric, malic, maleic, tartaric, citric, benzoic, methanesulfonic or carbonic acids.

The compounds of general formula (1) possess useful pharmaceutical properties. In particular they possess useful antiepileptic and sedative properties. These activities were assessed by standard methods. Antiepileptic activity was measured by assessing a compound's ability to prevent the hind limb tonic extension component of the seizure in groups of mice induced by maximal electroshock (MES) after oral or intraperitoneal administration according to the procedures of the Epilepsy Branch, NINCDS as published by R. J. Porter, et al., *Cleve. Clin. Quarterly*, 1984, 51, 293, and compared to the standard agents dilantin and phenobarbital. Activities ($ED_{50}$'s) in the range of 10–400 m/k after oral administration in this assay system were obtained. Sedative activity was assessed by behavioral observation in groups of mice. Selected compounds exhibited activity in the range of 30–600 m/k in this assay.

An important factor in judging the usefulness of antiepileptic agents is an evaluation of their propensity to produce neurotoxic effects (R. J. Porter, *Cleve. Clin. Quarterly*, 1984, 51, 293). Selected compounds were evaluated in an acute neurological impairment (NI) assay and $NI_{50}$ doses determined in mice essentially according to the procedure of Coughenour, et al., *Pharmac. Biochem. Behav.*, 1977, 6, 351. The oral therapeutic index (TI), that is, the $NI_{50}$ in the neurological impairment assay divided by the $ED_{50}$ in the maximal electroshock assay after oral doses, was calculated. High oral therapeutic indices were observed.

The following non-limiting illustrations and examples are provided to exemplify the preparation of the intermediate amines of formula (2) and their conversion to the novel compounds of general formula (1).

PREPARATION OF INTERMEDIATES

ILLUSTRATION 1

Preparation of 1,2-Diphenyl-2-propylamine hydrochloride

This compound was prepared by suitable modification of the procedures described by Christol, *Bull Soc. Chim. Fr.*, 1963, 4, 877, and Ho and Smith, *Tetrahedron*, 1970, 26, 4277 as follows. To a suspension of sodium cyanide (34.3 g, 0.7 mol) in 500 ml of glacial acetic acid and 100 ml of n-butylether at 0° C. was added portionwise 200 ml of concentrated sulfuric acid. The ice bath was removed and a solution of 1,2-diphenyl-2-propanol (106 g, 0.5 m) in 100 ml of n-butylether was added dropwise over a period of 2 hours, then the mixture stirred for 48 hours. The mixture was poured into 1000 ml of ice, and extracted with chloroform. The extracts were washed with water, dried and evaporated to a solid residue which was stirred with hexane (500 ml), filtered and dried to give 85.35 g (72% yield) of N-formyl-1,2-diphenyl-2-propylamine, mp 97°–99° C. This was suspended in 1L of 10% HCl and heated to reflux for 2.5 hours. After cooling in air for 1 hour then in an ice bath for 30 minutes, the white solid which had crystallized was collected by filtration and vacuum dried to give 85.9 g (97% yield) of 1,2-diphenyl-2-propylamine hydrochloride, mp 175°–178° C.

ILLUSTRATION 2

Preparation of 1,2-bis-(4-fluorophenyl)-2-propylamine hydrochloride

By procedures essentially the same as those described in Illustration 1, and by substituting 1,2-bis(4-fluorophenyl)-2-propanol (prepared by the reaction of 4-fluorobenzyl magnesium chloride and 4'-fluoroacetophenone) for 1,2-diphenyl-2-propanol; the corresponding 1,2-bis(4-fluorophenyl)-2-propylamine hydrochloride, mp 188°–189° C., was prepared.

ILLUSTRATION 3

Preparation of 1,2-Diphenyl-2-butylamine hydrochloride

By procedures essentially the same as those described in Illustration I, and by substituting 1,2-diphenyl-2-butanol (prepared by the reaction of benzylmagnesium chloride and propiophenone) for 1,2-diphenyl-2-propanol; the corresponding 1,2-diphenyl-2-butylamine hydrochloride, mp 190°–192.5° C., was prepared.

ILLUSTRATION 4

Preparation of (−)-1,2-diphenyl-2-propylamine

Racemic 1,2-diphenyl-2-propylamine (86 g, 0.4 mol) was dissolved in 0.5L 95% ethanol, heated to near reflux and added to a solution of (−)-dibenzoyltartaric acid monohydrate (151.9 g, 0.4 mol) in 0.5L 95% ethanol also at reflux. A white solid crystallized immediately. The mixture was refluxed for 5 minutes, then allowed to cool to ambient temperature. The solid was collected by filtration and dried to give 86.2 g $[\alpha]_D = -94.2°$ (C=0.5, $CH_3OH$). The filtrate was saved. The solid was suspended in 0.9L of 95% ethanol, stirred and heated to reflux for 1 hour, allowed to cool to ambient temperature and the white solid collected by filtration and vacuum dried at 80° C. for 8 hours to give 60.2 g of (−)-1,2-diphenyl-2-propylamine (−)-dibenzoyl tartrate, mp 194°–195° C., $[\alpha]_D = -96.0°$ (C=0.5, $CH_3OH$). 5.0 g of this salt was dissolved in 250 ml $CHCl_3$ and 200 ml 5% $NH_4OH$ shaken vigorously, the layers separated and the organic phase washed with 3×200 ml 5% $NH_4OH$, 2×200 ml $H_2O$ and dried over $MgSO_4$. The solvent was evaporated to give 1.75 g of (−)-1,2-diphenyl-2-propylamine as an oil. The maleate salt was prepared by dissolving this oil in 25 ml of ethyl acetate and adding the solution to a hot solution of maleic acid (1.02 g, 8.87 mmol) in 50 ml of 3/1 ethyl acetate/isopropanol. Upon cooling a white solid crystallized, which was collected by filtration and vacuum dried to give 2.05 g of (−)-1,2-diphenyl-2-propylamine maleate, mp. 176°–177° C., $[\alpha]_D = -27.4°$ (C=1, $CH_3OH$).

ILLUSTRATION 5

Preparation of (+)-1,2-Diphenyl-2-propylamine

The filtrate residue which was saved in Illustration 4, was treated with 1L $CHCl_3$ and 0.9L 5% $NH_4OH$, shaken vigorously, the layers separated and the organic phase washed with 4×800 ml 5% $NH_4OH$ and 2×500 ml $H_2O$, then dried over $MgSO_4$ and evaporated to an oil 32.3 g, which is enriched in (+)-1,2-diphenyl-2-propylamine. This oil (32.3 g, 0.153 mol) was dissolved in 200 ml hot 95% ethanol and added to a stirred solution of (+)-dibenzoyl tartaric acid monohydrate (57.55 g, 0.153 mol) in 600 ml of refluxing 95% ethanol. A white solid crystallized immediately, which was stirred at reflux for 5 minutes, then allowed to cool to ambient temperature. The solid was collected by filtration and vacuum dried at 80° C. for 8 hours to give 71.6 g of (+)-1,2-diphenyl-2-propylamine (+)-dibenzoyltartrate, mp 197°–198° C., $[\alpha]_D = +95.8°$ (C=0.5, $CH_3OH$). 5.0 g of this salt was dissolved in 250 ml $CHCl_3$ and 200 ml 5% $NH_4OH$, shaken vigorously, the layers separated and the organic phase washed with 3×200 ml 5% $NH_4OH$ and 2×200 ml $H_2O$ and dried over $MgSO_4$. The solvent was evaporated to give 1.75 g of (+)-1,2-diphenyl-2-propylamine as an oil. The maleate salt was prepared by dissolving this oil in 25 ml ethyl acetate and adding the solution to a hot solution of maleic acid (1.02 g, 8.78 mmole) in 50 ml 3/1 ethyl acetate/isopropanol. Upon cooling a white solid crystallized, which was collected by filtration and vacuum dried to give 2.06 g of (+)-1,2-diphenyl-2-propylamine maleate, mp 177°-178° C., $[\alpha]_D = +27.3°$ (C=1, CH$_3$OH).

ILLUSTRATION 6

Preparation of N-Methyl-1,2-diphenyl-2-propylamine hydrochloride

N-formyl-1,2-diphenyl-2-propylamine (23.6 g, 0.1 mol) was added to a stirred suspension of LiAlH$_4$ (15.0 g, 0.395 mol) in 1L of dry tetrahydrofuran. After 2 hours the mixture was heated at 35° C. for 22 hours, then refluxed for 2 hours, and allowed to cool to room temperature. Water was added to decompose the excess LiAlH$_4$, and the mixture filtered to remove the solid salts. Evaporation of the solvent gave 23.0 g of the crude product as a yellow oil. This was dissolved in 180 ml of ethyl acetate and 20 ml of isopropanol and acidified with HCl gas. Upon standing a white solid crystallized which was collected by filtration and vacuum dried at 65° C. to give 21.7 g (84%) of N-methyl-1,2-diphenyl-2-propylamine hydrochloride, mp 200°-201° C.

EXAMPLE 1

Preparation of 2-Methylamino-N-(1,2-diphenyl-1-methylethyl)-propanamide hydrochloride To a stirred solution of 1,2-diphenyl-2-propylamine (10.35 g, 0.049 mol) in 400 ml of chloroform under nitrogen were added N-CBZ-N-methyl-DL-alanine (11.62 g, 0.049 mol) and then a solution of dicyclohexylcarbodiimide (10.11 g, 0.049 mol) in 125 ml of chloroform, and the mixture was stirred for 24 hrs. The precipitated solid was removed by filtration and the solvent was evaporated. The residue was treated with ethyl acetate (100 ml), filtered, an additional 300 ml of ethyl acetate added, and then washed with 1% cold HCl (2×250 ml), dried over MgSO$_4$, and the solvent evaporated. The residue (21.07 g) was dissolved in 350 ml of methanol and 35 ml of 10% HCl and hydrogenated at 40 psi in a Parr apparatus over 3.0 g of 10% Pd/C catalyst for 3 hrs. The catalyst was removed by filtration, the solvents evaporated, and the residue dissolved in water (200 ml) and chloroform (200 ml), basified to pH 11 with 50% NaOH, shaken, and separated. The aqueous phase was extracted with chloroform (2×200 ml) and the combined organic phases washed with water (300 ml) and dried over MgSO$_4$. Removal of solvent gave 13.7 g of a pale yellow oil. This oil was dissolved in 2-propanol (200 ml) and treated with gaseous HCl. The white solid obtained was recrystallized from 2-propanol (200 ml) and methanol (20 ml) to give 6.92 g of 2-methylamino-N-(1,2-diphenyl-1-methylethyl)-propanamide hydrochloride, mp. 275°-276° C.

EXAMPLE 2

Preparation of 2-(Methylamino)-N-(1,2-diphenyl-1-methylethyl)-acetamide hydrochloride To a stirred solution of 1,2-diphenyl-2-propylamine hydrochloride (77 g, 0.31 mol) in 820 ml of chloroform at 0° C., was added triethylamine (131 g, 1.3 mol) and then chloroacetyl chloride (36.9 g, 0.326 mol) and the mixture stirred under nitrogen for 24 hrs. 10% HCl (1L) was added, stirred for 1 hr then the layers separated. The chloroform layer was washed with 10% HCl (2×500 ml), water (2×500 ml), dried, and evaporated to a tan solid, 92.0 g. This was slurried in 700 ml of hot cyclohexane, filtered, then slurried in 500 ml of hexane, filtered and dried to give 56 g of the chloroacetamide as a tan solid, mp. 161°-162° C. The chloroacetamide (10 g, 0.035 mol) was added portionwise to a stirred solution of monomethylamine (25 ml) in 250 ml of methanol 0° C., the mixture was treated with 25 ml chloroform and allowed to warm to room temperature and stirred for 23 hrs. All solids were not dissolved so 25 ml of monomethylamine and 50 mls chloroform were added and the mixture stirred for 85 hrs, then evaporated to a brown residue. This was dissolved in water (150 ml) and chloroform (100 ml), basified to pH 11 with 50% NaOH, shaken, layers separated, the aqueous phase extracted with chloroform (2×200 ml) and the combined organic phases washed with water (250 ml), dried, and evaporated to a brown residue. This was treated with 250 ml of hexane, stirred vigorously, and the hexane soluble materials decanted from some dark brown residue. The hexane was evaporated and the oily residue dissolved in ethyl acetate (49 ml) and isopropanol (10 ml), cooled to 0° C. and acidified with HCl gas. The solid salt crystallized and was recrystallized twice from 100 ml of isopropanol and 25 ml of ethyl acetate, and dried to give 6.0 g of 2-(methylamino)-N-(1,2-diphenyl-1-methylethyl)acetamide hydrochloride, mp. 225°-226° C.

EXAMPLE 3

Preparation of 2-(Ethylamino)-N-(1,2-diphenyl-1-methylethyl)-acetamide hydrochloride By procedures essentially the same as those described in Example 2 and by substituting ethylamine for monomethylamine; the corresponding 2-(ethylamino)-N-(1,2-diphenyl-1-methylethyl)acetamide hydrochloride, mp. 164°-165° C., was prepared.

EXAMPLE 4

Preparation of 2-(Propylamino)-N-(1,2-diphenyl-1-methylethyl)-acetamide hydrochloride By procedures essentially the same as those described in Example 2 and by substituting n-propylamine for monomethylamine; the corresponding 2-(propylamino)-N-(1,2-diphenyl-1-methylethyl)acetamide hydrochloride, mp. 188°-189° C., was prepared.

EXAMPLE 5

Preparation of 2-(2-Propylamino)-N-(1,2-diphenyl-1-methylethyl)acetamide hydrochloride By procedures essentially the same as those described in Example 2 and by substituting isopropylamine for monomethylamine; the corresponding 2-(2-propylamino)-N-(1,2-diphenyl-1-methylethyl)acetamide hydrochloride, mp. 191° C., was prepared.

EXAMPLE 6

Preparation of 2-(Cyclopropylamino)-N-(1,2-diphenyl-1-methylethyl)acetamide hydrochloride By procedures essentially the same as those described in Example 2 and by substituting cyclopropylamine for monomethylamine, the corresponding 2-(cyclopropylamino)-N-(1,2-diphenyl-1-methylethyl)-acetamide hydrochloride, mp. 194°-195° C., was prepared.

EXAMPLE 7

Preparation of
2-(Butylamino)-N-(1,2-diphenyl-1-methylethyl)-acetamide hydrochloride By procedures essentially the same as those described in Example 2 and by substituting n-butylamine for monomethylamine; the corresponding 2-(butylamino)-N-(1,2-diphenyl-1-methylethyl)acetamide hydrochloride, mp. 192° C., was prepared.

EXAMPLE 8

Preparation of
2-(Hexylamino)-N-(1,2-diphenyl-1-methylethyl)-acetamide hydrochloride By procedures essentially the same as those described in Example 2 and by substituting n-hexylamine for monomethylamine; the corresponding 2-(hexylamino)-N-(1,2-diphenyl-1-methylethyl)acetamide hydrochloride, mp. 201°-210° C., was prepared.

EXAMPLE 9

Preparation of
2-(Methylamino)-N-methyl-N-(1,2-diphenyl-1-methylethyl)acetamide hydrochloride By procedures essentially the same as those described in Example 2 and by substituting N-methyl-1,2-diphenyl-2-propylamine hydrochloride for 1,2-diphenyl-2-propylamine hydrochloride; the corresponding 2-(methylamino)-N-methyl-N-(1,2-diphenyl-1-methylethyl)-acetamide hydrochloride, mp. 205° C., was prepared.

EXAMPLE 10

Preparation of
(+)-2-(Methylamino)-N-(1,2-diphenyl-1-methylethyl)acetamide hydrochloride By procedures essentially the same as those described in Example 2 and by substituting (+)-1,2-diphenyl-2-propylamine hydrochloride for 1,2-diphenyl-2-propylamine hydrochloride; the corresponding (+)-2-(methylamino)-N-(1,2-diphenyl-1-methylethyl)acetamide hydrochloride, mp. 170.5°-172.5° C., was prepared.

EXAMPLE 11

Preparation of
(−)-2-(Methylamino)-N-(1,2-diphenyl-1-methylethyl)acetamide

By procedures essentially the same as those described in Example 2 and by substituting (−)-1,2-diphenyl-2-propylamine for 1,2-diphenyl-2-propylamine; the corresponding (−)-2-(methylamino)-N-(1,2-diphenyl-1-methylethyl)acetamide hydrochloride, mp. 171°-172.5° C., was prepared.

EXAMPLE 12

Preparation of
2-(Methylamino)-N-[1,2-bis(4-fluorophenyl)-1-methylethyl]acetamide hydrochloride To a stirred solution of 1,2-bis(4-fluorophenyl)-2-propylamine (11.08 g, 0.045 mol) and triethylamine (9.11 g, 0.09 mol) in 130 ml of chloroform under nitrogen at 0° C. was added dropwise a solution of chloroacetyl chloride (5.31 g, 0.047 mol) in 15 ml of chloroform. The ice bath was removed and the mixture stirred for 19 hrs, then poured into 200 ml of 10% HCl. The layers were separated, the organic layer washed with 10% HCl (2×80 ml), water (2×70 ml), dried, and evaporated to a brown residue. This was dissolved in 250 ml cyclohexane (200 ml) and drying gave 3.57 g of the chloroacetamide, mp. 156°-157° C. 10.0 g of material obtained as above (0.031 mol) was added portionwise to a stirred solution of monomethylamine (35 ml) in 250 ml of methanol at 0° C. The ice bath was removed and the mixture stirred for 48 hrs. The solvent was evaporated and the residue dissolved in chloroform (350 ml) and water (200 ml) and basified to pH 11 with 50% NaOH. Layers were separated, the aqueous layer extracted with chloroform (2×200 ml), and the combined organic layers were washed with water (2×150 ml), dried and evaporated to a brown oil. This was dissolved in 175 ml of ethyl acetate, acidified with HCl saturated isopropanol, and the crystallized solid collected by filtration. Recrystallization from 175 ml of ethyl acetate, 15 ml of methanol and 10 ml of ethanol, and vacuum drying gave 4.54 g of 2-(methylamino)-N-[1,2-bis(4-fluorophenyl)-1-methylethyl]acetamide hydrochloride, mp 250°-251° C.

EXAMPLE 13

Preparation of
2-(Butylamino)-N-[1,2-bis(4-fluorophenyl)-1-methylethyl]acetamide hydrochloride By procedures essentially the same as those described in Example 12 and by substituting n-butylamine for monomethylamine; the corresponding 2-butylamino-N-[1,2-bis(4-fluorophenyl)-1-methylethyl]acetamide hydrochloride, mp. 131°-132° C., was prepared.

EXAMPLE 14

Preparation of
2-(Methylamino)-N-(1-ethyl-1,2-diphenylethyl)-acetamide hydrochloride By procedures essentially the same as those described in Example 2 and by substituting 1,2-diphenyl-2-butylamine hydrochloride for 1,2-diphenyl-2-propylamine hydrochloride; the corresponding 2-(methylamino)-N-(1-ethyl-1,2-diphenylethyl)acetamide hydrochloride, mp. 230°-231.5° C., was prepared.

EXAMPLE 15

Preparation of
2-(Butylamino)-N-(1-ethyl-1,2-diphenylethyl)-acetamide hydrochloride By procedures essentially the same as those described in Example 2 and by substituting 1,2-diphenyl-2-butylamine hydrochloride for 1,2-diphenyl-2-propylamine hydrochloride and substituting n-butylamine for monomethylamine; the corresponding 2-butylamino-N-(1-ethyl-1,2-diphenylethyl)-acetamide hydrochloride, mp. 202°-205° C., was prepared.

I claim:
1. A compound having the formula:

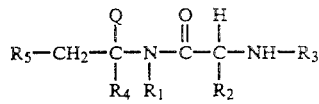

wherein $R_4$ is lower alkyl ($C_1$–$C_4$), $R_1$ is hydrogen or methyl, $R_2$ is hydrogen or methyl, $R_3$ is lower alkyl ($C_1$–$C_6$) or cyclopropyl, and where $R_5$ and Q are independently selected from phenyl or 4-fluorophenyl, and pharmaceutically acceptable acid addition salts thereof.

2. A compound according to claim 1 wherein the compound is 2-methylamino-N-(1,2-diphenyl-1-methylethyl)propanamide hydrochloride.

3. A compound according to claim 1 wherein the compound is 2-methylamino-N-(1,2-diphenyl-1-methylethyl)acetamide hydrochloride.

4. A compound according to claim 1 wherein the compound is 2-ethylamino-N-(1,2-diphenyl-1-methylethyl)acetamide hydrochloride.

5. A compound according to claim 1 wherein the compound is 2-propylamino-N-(1,2-diphenyl-1-methylethyl)acetamide hydrochloride.

6. A compound according to claim 1 wherein the compound is 2-(2-propylamino)-N-(1,2-diphenyl-1-methylethyl)acetamide hydrochloride.

7. A compound according to claim 1 wherein the compound is 2-(cyclopropylamino)-N-(1,2-diphenyl-1-methylethyl)acetamide hydrochloride.

8. A compound according to claim 1 wherein the compound is 2-(butylamino)-N-(1,2-diphenyl-1-methylethyl)acetamide hydrochloride.

9. A compound according to claim 1 wherein the compound is 2-(hexylamino)-N-(1,2-diphenyl-1-methylethyl)acetamide hydrochloride.

10. A compound according to claim 1 wherein the compound is 2-methylamino-N-methyl-N-(1,2-diphenyl-1-methylethyl)acetamide hydrochloride.

11. A compound according to claim 1 wherein the compound is (+)-2-(methylamino)-N-(1,2-diphenyl-1-methylethyl)acetamide hydrochloride.

12. A compound according to claim 1 wherein the compound is 2-(methylamino)-N-[1,2-bis(4-fluorophenyl)-1-methylethyl]-acetamide hydrochloride.

13. A compound according to claim 1 wherein the compound is 2-(butylamino)-N-[1,2-bis(4-fluorophenyl)-1-methylethyl]-acetamide hydrochloride.

14. A compound according to claim 1 wherein the compound is 2-(methylamino)-N-(1-ethyl-1,2-diphenylethyl)acetamide hydrochloride.

15. A compound according to claim 1 wherein the compound is 2-(butylamino)-N-(1-ethyl-1,2-diphenylethyl)acetamide hydrochloride.

* * * * *